United States Patent [19]

Enami et al.

[11] Patent Number: 5,264,359
[45] Date of Patent: Nov. 23, 1993

[54] METHODS FOR LARGE-SCALE CULTIVATION OF ANIMAL CELLS AND FOR MAKING SUPPORTING SUBSTRATA FOR THE CULTIVATION

[75] Inventors: Junpei Enami, Oaza-Kitakobayashi; Naohito Kondo, Yao; Toshikazu Takano, Ikoma; Kaneo Suzuki, Kashihara, all of Japan

[73] Assignee: Nitta Gelatin Inc., Osaka, Japan

[21] Appl. No.: 449,843

[22] PCT Filed: Apr. 13, 1989

[86] PCT No.: PCT/JP89/00404

§ 371 Date: Dec. 11, 1989

§ 102(e) Date: Dec. 11, 1989

[87] PCT Pub. No.: WO89/10397

PCT Pub. Date: Nov. 2, 1989

[30] Foreign Application Priority Data

Apr. 18, 1988 [JP] Japan .................. 63-96528

[51] Int. Cl.$^5$ ............... C12N 5/00; C12N 11/02; C12N 11/10; C12N 11/14

[52] U.S. Cl. ..................... 435/240.23; 435/176; 435/177; 435/178; 435/179; 435/180; 435/182; 435/240.243; 435/240.23

[58] Field of Search ............... 435/176, 177, 178, 179, 435/180, 182, 240.243, 240.23

[56] References Cited

U.S. PATENT DOCUMENTS

| | | | |
|---|---|---|---|
| 4,352,883 | 10/1982 | Lim | 435/178 |
| 4,373,027 | 2/1983 | Berneman | 435/240 |
| 4,409,331 | 10/1983 | Lim | 435/178 |
| 4,495,288 | 1/1985 | Jarvis, Jr. | 435/241 |
| 4,565,580 | 1/1986 | Miyata et al. | 106/124 |

FOREIGN PATENT DOCUMENTS

| | | |
|---|---|---|
| 0173915 | 3/1986 | European Pat. Off. |
| 0258441 | 3/1988 | European Pat. Off. |
| 2094832 | 9/1982 | United Kingdom |
| 83/03102 | 9/1983 | World Int. Prop. O. |
| 85/05630 | 12/1985 | World Int. Prop. O. |
| 86/05811 | 10/1986 | World Int. Prop. O. |
| WO87/00197 | 1/1987 | World Int. Prop. O. |

OTHER PUBLICATIONS

Chemical Abstracts, vol. 92, No. 25, Jun. 23, 1980, p. 417, Abstract No. 212933f.
Chemical Abstracts, vol. 97, No. 11, Sep. 13, 1982, p. 402, Abstract No. 88225p.
Chemical Abstracts, vol. 100, No. 21, May 21, 1984, p. 429, Abstract No. 172386e.
Chemical Abstracts, vol. 101, No. 11, Sep. 10, 1984, p. 400, Abstract No. 87917e.
Biological Abstracts No. 76039245 (1982).
Japanese Patent Gazette (Kokai) No. 62-502936, dated Nov. 26, 1987.
Japanese Patent Gazette (Kokai) No. 55-157502, dated Dec. 8, 1980.
Japanese Patent Gazette (Kokai) No. 62-25974, dated Feb. 3, 1987.
Japanese Patent Gazette (Kokai) No. 63-3786, dated Jan. 8, 1988.
Japanese Patent Gazette (Kokai), No. 59-21388, dated Feb. 3, 1984.
Japanese Patent Gazette (Kokai) No. 62-175172, dated Jul. 31, 1987.
Japanese Patent Gazette (Kokai) No. 62-171680, dated Jul. 28, 1987.
Japanese Patent Gazette (Kokai) No. 63-209581, dated Aug. 31, 1988.
Keese et al. Science vol. 219 pp. 1448-1449 1983.

*Primary Examiner*—Michael G. Wityshyn
*Assistant Examiner*—Ralph Gitomer
*Attorney, Agent, or Firm*—Armstrong, Westerman, Hattori, McLeland & Naughton

[57] ABSTRACT

A method for the large-scale cultivation of animal cells wherein animal cells are embedded in a collagen gel which is covered by a protective coating. The protective coating supports and protects the collagen matrix.

2 Claims, 2 Drawing Sheets

METHODS FOR LARGE-SCALE CULTIVATION OF ANIMAL CELLS AND FOR MAKING SUPPORTING SUBSTRATA FOR THE CULTIVATION

TECHNICAL FIELD

The present invention relates to methods for the large scale cultivation of animal cells and for making supporting substrata for the cultivation.

BACKGROUND ART

Animal cells are classified into two categories: (1) anchorage-dependent cells, which grow or proliferate only after attachment to supporting substrata, and (2) anchorage-independent cells, which do not require attachment to supporting substrata and can grow even in a suspension state. The method for the large scale cultivation of anchorage-dependent cells differs from that for anchorage-independent cells in requiring a suitable supporting substrate for cell attachment. Various kinds of two- and three-dimensional culture methods, depending on differences in the supporting substrate structure or the substrate material used, have been proposed (Japanese national publication of translation of international application, showa 62-502936 (International publication number WO 86/05811), Cytodex (commercial name for a product from Pharmacia Fine Chemicals Co., Ltd.), and Japanese official patent provisional publication, showa 63-209581).

In the two-dimensional culture methods, animal cells attach to the surface of the supporting substrate and grow on the surface to form a monolayer of cells. A number of two-dimensional culture methods have been proposed, the purpose of which is to increase cell density of the cultured cells, enhance product secretion in cultured cells, simplify recovery and purification of cultivated products, and the like.

Some of the present inventors have proposed a large-scale cultivation method wherein anchorage-dependent animal cells are cultured three-dimensionally using collagen gels as supporting substrata (Japanese official patent provisional publication, showa 62-175172; Japanese official patent provisional publication, showa 62-171680; International publication number WO 87/04458; U.S. Ser. No. 110,749; and the European patent application, publication number 0258441). In this method, the cells are embedded in collagen gels and grow three-dimensionally in the gels. By using collagen, it is possible to make the in vitro surroundings very close to the in vivo surroundings. As such, the collagen gel culture method has made it possible to culture some kinds of cells which are unable to be cultured by monolayer culture methods and by three-dimensional culture methods using supporting substrata other than collagen. Therefore, compared to two-dimensional culture methods and methods using other three-dimensional substrata, the three-dimensional culture method using collagen gel is not only advantageous in that producibility arising from an increase in cell attachment area is increased, which is due to the fact that it is three-dimensional, and with respect to the simplicity of culturing due to cell fixation, but is also advantageous due to the increase in the kind of cells which may be cultured.

Considering these advantages, the present inventors have studied the development of a method for large-scale cultivation in which animal cells are embedded in collagen gels and cultured three-dimensionally. As a result of the present inventors' studies, it was found that this type of culture method has at least one problem among the following (1)-(3).

(1) If the collagen gel is soft, it is hard to handle and apt to be damaged.

(2) As the collagen gel shrinks with cell growth, long-term cultivation is impossible.

(3) While problems (1) and (2) may be solved when a collagen gel of high gel strength is used as a supporting substrate, if gel strength is high, new problems appear, such as a decrease in the cultivation rate of cells or a limitation of the kind of animal cells possible to be cultivated.

These problems not only adversely affect the convenience of the treatment, but also adversely affect cell growth.

Accordingly, the first object of the invention is to provide a method for the large-scale cultivation of animal cells wherein the collagen gels in which the animal cells are embedded are easily handled, shrinkage of the collagen gels which accompanies cell growth can be prevented, and collagen gels having a suitable gel strength as supporting substrata can be used. The second object of the invention is to provide a method of easily producing supporting substrata for use in a method for the large-scale cultivation of animal cells.

DISCLOSURE OF INVENTION

The first object of the invention has been solved by employing a method for the large-scale cultivation of animal cells which is characterized by the use of a collagen gel (in which animal cells are embedded) covered by a protective coating, the gel being supported with a protective coating. The protective coating protects the collagen gel inside the coating and thereby its gel shape is kept. For this reason, the collagen gel with a gel strength suitable for a cell to be cultivated can be used. Further, since the collagen gel in which animal cells are embedded is supported with said protective coating from the outside, the collagen gel does not shrink with cell proliferation (which have already produced a great number of cells), so that cell proliferation is maintained for a long period.

The second object of the invention has been solved by producing a supporting substrate for the large-scale cultivation of animal cells by a process which is characterized by feeding a collagen solution in which animal cells are suspended and a coating-forming agent solution forming a protective coating at the same time from the inner and outer tubes of a double layer nozzle, respectively, and then, after the collagen solution is covered with the coating-forming agent solution, the coating-forming agent solution is hardened by putting it in a hardening solution to make a protective coating and to undergo gelation, and thereby said animal cells are embedded in a collagen gel being covered with the protective coating. By expelling a collagen solution suspended with animal cells and a coating-forming agent solution from a double layer nozzle, the collagen solution suspended with animal cells comes in contact with the coating-forming agent solution in a solution state and becomes covered by the coating-forming agent solution. Under this condition, the coating-forming agent solution is hardened in the hardening solution to make a protective coating.

The collagen is a favored agent for the formation of a supporting substrate. Since collagen is a fiber protein existing everywhere in the animal body, it can create in vivo surroundings in vitro (outside of the living body) by being transformed into a gel and being used as a supporting substrate for a cell. The kind of collagen being used for this invention is not especially limited and various types of collagens can be used.

Collagen is used as a solution. The collagen solution is prepared so as to have a physiological salt concentration and pH and the animal cells are suspended in the collagen solution. To prepare a collagen gel using this collagen solution and to embed the cells in the gel, the collagen solution is transformed into a gel, for example with warming at 25°-37° C. and the cell suspension is embedded in the collagen gel. The collagen solution can be treated by adding, if necessary, various components (for example, a physiologically active substance such as a serum, a cell-growing factor, and a hormone, etc.).

An animal cell embedded in a collagen gel allows for the support of a cell undergoing anchorage-dependent proliferation and brings the cell close to the in vivo surroundings in order that the cell can be proliferated in a three-dimensional way. In this way, the cell can be proliferated in a three-dimensional way, it can be cultivated in high density, in large quantity and also, for a long period as compared with previous methods. In addition, cell differentiation can be derived.

The collagen gel, as far as it has a shape suitable for large-scale cultivation, is not especially limited in shape. For example, particle shapes such as a sphere, a cylinder, an ellipsoid, a cube, a rectangular parallelepiped shape, and an indefinite shape, etc., a noodle shape, a sheet shape, and so forth may be used. If it is a particle shape, since a surface area per volume can be enlarged, it is profitable for material exchange between the inside and outside. The shape size is not especially limited and, for example, preferred is a range of 0.1-10 mm in length and side directions, respectively. If the size is larger than this range, there is a possibility that either transmission of a nutrition component or a superannuated product or gas exchange through the protective coating between collagen gel and the outside cultivating solution is delayed or does not take place at all, and the cell proliferation may be disturbed. If smaller than this range, the cultivating solution when it is exchanged, may have a solid floating and dispersed in it such that, at filtering, blocking takes place. A collagen gel attaching to a protective coating is preferred to have a bead shape of 3 mm or less in diameter or a related shape. This is because, when the cultivating solution is exchanged, the collagen gel is sufficient in size for easy separation from a cultivating solution where the collagen gel is soaked, and the material exchange between an inside and an outside of the collagen gel becomes facile. According to the method for large-scale cultivation of animal cells in the present invention, it is possible to cultivate a large quantity of cells in a small space and also, to take out with high efficiency a cell or a product.

The protective coating, which protects and supports the collagen gel, is favorable if it has such properties as hardness, capability of hardening in a short period of time, absence of toxicity against cells, and facile transmission of a nutrition component into the cultivating solution and a metabolite (or a product) of cells. It is also favorable if the protective coating can be dissolved again under conditions such that the cell is not damaged, so that the cell can be recovered alive following cultivation.

Although the protective coating is not especially defined, for example, a coating is used which is prepared in a thin-layer state by hardening of a high molecular weight compound such as alginic acid, alginic acid salt, carrageenan, locust bean gum, chitin, a chitin derivative, agarose, polyurethane, polylysine, and polyvinyl alcohol (in this invention a high molecular weight compound of these kinds is called "a coating-forming agent"). The coating-forming agent is not especially defined, if it is capable of hardening under a condition that a cell is not damaged and also, is harder than a collagen gel. Besides, from a point of that a jointing force between the collagen gel and the protective coating is further increased, preferred is the one having superior affinity with collagen as a coating-forming agent. Thickness of the protective coating is not especially defined, preferred is to be in a range of 0.01-10 mm and more preferred is to be in a range of 0.1-1.0 mm. If the protective coating is thicker than the upper limit of the range, the material exchange may be disturbed. If thinner than the lower limit, sufficient formation of a protective coating becomes difficult and, even if the coating is formed, there may be a case that the coating is damaged or the collagen shrinkage is not stopped.

The protective coating is preferred to cover 50% or more of the total surface of the collagen gel, and more preferably 100%. If the covering is less than 50%, physical strength is weak and handling becomes difficult.

When a collagen gel attached to a protective coating and formed in a noodle or a sheet shape is cut after forming, the covering percentage becomes less than 100%. In addition, when the protective covering percentage is less than 50%, collagen gel shrinkage sometimes cannot be prevented.

The protective coating is obtained, for example, by wrapping the outside surface of a collagen gel in which animal cells are embedded or a drop of a collagen solution suspended with animal cells in a coating-forming agent solution used for the formation of the protective coating. The coating-forming agent solution is then hardened. When the outside surface of a drop of a collagen solution is wrapped in a coating-forming agent solution, the collagen solution undergoes gelation after the protective coating is formed or together with coating formation. The protective coating covers the collagen gel, firmly joints with it, and supports it from the outside. In this way, collagen shrinkage is prevented. Moreover, since the collagen gel is covered with the protective coating, even if it collides with or comes in contact with other things, the animal cell as well as the collagen gel are protected.

The coating-forming agent solution may contain only one coating-forming agent, or may contain the coating-forming agent together with other kinds of coating-forming agents, a buffer solution, a culture solution, a serum, or other additives.

Hardening of the coating-forming agent solution can be carried out in any way, for example, by putting in a hardening solution. This hardening solution is properly prepared according to the kind of coating-forming agent solution used. Depending upon the hardening condition for the coating-forming agent solution, the hardening solution is used by suitably selecting from, for example, a salt solution, a cross-linking agent solution, or water (for example, cold water, etc.). A preferred hardening solution is one which does no damage to the cells. If the coating-forming agent solution is a sodium alginate solution, a hardening solution containing a two-valent metallic ion or a hardening solution made by a polycation such as chitin and chitosan is used. Especially, a calcium ion is used as a metallic ion. If the coating-forming agent solution is a solution of sodium alginate, and for example, in a case of continuous gel formation where the below-described double layer nozzle is used, gelation rapidly proceeds with a calcium ion of 50-70 mM (millimoles). When a chitosan solution is used as a hardening solution for an aqueous solution of sodium alginate, a thin membrane is rapidly formed on a dropped particle surface by reaction of the chitosan with alginic acid. A membrane having a strength sufficient for operation can be formed within a short time. The membrane is also capable of further supporting an alginic acid gel from the outside.

When alginic acid, alginic acid salt, and salts of alginic acid derivatives, etc., are used as a coating-forming agent, a compound undergoing rapid gelation with a calcium ion of 0.1M or less is favorably used. This is because calcium ion concentration of this order is in a range similar to that of a living body (the in vivo surroundings) or is in a range wherein the cells will not be damaged.

In the present invention, the hardening comprises not only gelation of the above-describe natural high molecular weight substance, but also formation of a cross-linking structure of the synthetic high molecular weight substance.

Since the protective coating and the collagen gel both are able to contain a large amount of water, material exchange between the inside and outside (for example, breathing, intake of nutrition, excretion, and release of secretion, etc.) is possible and suitable for cultivating a cell. For example, if the protective coating is a product obtained from hardening of said natural high molecular weight substance, said product is a gel and is able to hold a large amount of water. If the protective coating is a product obtained from hardening of a polyurethane, since a number of fine continuous pores are formed by carbon dioxide gas generated during hardening, a large amount of water can be held in the pores. Also, if the protective coating is a polylysine or a polyvinyl alcohol, a large amount of water can be held in a cross-linking structure of these products obtained from hardening.

To carry out the large-scale cultivation of animal cells, animal cells embedded in a collagen gel, which is covered with a protective coating, can be prepared using a double layer nozzle composed of an inner tube and an outer tube. A collagen solution suspended with animal cells is supplied continuously or intermittently to the inner tube through a pipe, etc., and, at the same time, a coating-forming agent solution is supplied continuously to the outer tube through a pipe, etc., and then, from the double layer nozzle, both solutions are dropped or expelled with pushing. It is recommended that the double layer nozzle be installed in a tightly closed vessel. A double layer nozzle may be used (1) in which the front top of the inner tube is stretched longer than the front top of the outer tube, (2) in which both tops are the same length, or (3) in which the front top of the inner tube is shorter than the front top of the outer tube. The collagen solution leaving the inner tube is, in part or totally, wrapped by the coating-forming agent solution leaving the outer tube and takes a sphere or a noodle shape. Under these conditions, when the wrapped collagen solution of such a shape is put into the hardening solution, the coating-forming agent solution in the outer layer undergoes hardening to form a protective coating. Then, the thus-formed product is separated from the hardening solution and is washed by physiological salt solution (for example, a Hanks' solution) to remove metallic ion, such as an excessive calcium ion, etc. Then, the cultivation is performed with soaking in a cultivating solution and with stirring or circulating of the cultivating solution. Furthermore, the gelation of the collagen solution, if it is before cultivation, can be carried out at any time.

Cultivation is performed by soaking the collagen gel, in which animal cells are embedded and covered with a protective coating, in a cultivating solution. Components and concentration of the cultivating solution and cultivating temperature are set by properly selecting from those suitable for the embedded animal cells.

The means for large-scale cultivation are not especially limited. For example, proper stirring and exchanging of a culture solution using a bottle of a stirrer type, a bottle of a roller type, a bottle of a propeller type, or a bottle of an air agitation type, and proper filling and holding in a column capable of circulating a culture solution and then, circulating the solution in the column. Even if large-scale cultivation of this kind is used, the collagen gel is not damaged and the treatment is easy. Because of this, a large volume vessel can be used as a vessel to cultivate an animal cell and with good efficiency.

Furthermore, by mixing a heavy substance with a protective coating and/or a collagen gel, specific gravity can be adjusted and also, separation of cells from a cell-cultivating solution, when a culture solution is exchanged, can be easily done.

The method for large-scale cultivation of animal cells according to the invention exhibit the below-described effects (a)-(c).

(a) Since the collagen gel is protected by a protective coating, handling, such as transferring it to a cultivation apparatus, is easy and the gel is not easily damaged when a culture solution is exchanged or circulated.

(b) Since shrinkage of the collagen gel, which accompanies cell growth, is prevented, the cells can be maintained for a long time.

(c) Since effects (a) and (b) are obtained independent of the magnitude in gel strength of a collagen gel, a gel strength suitable for an animal cell to be cultivated can be chosen and thereby, the kind of animal cells possible to cultivate becomes wide.

BRIEF DESCRIPTION OF THE DRAWINGS

FIG. 1(a) is a longitudinal sectional view and FIG. 1(b) is a transverse sectional view.

BEST MODE FOR CARRYING OUT THE INVENTION

Figure 1A:
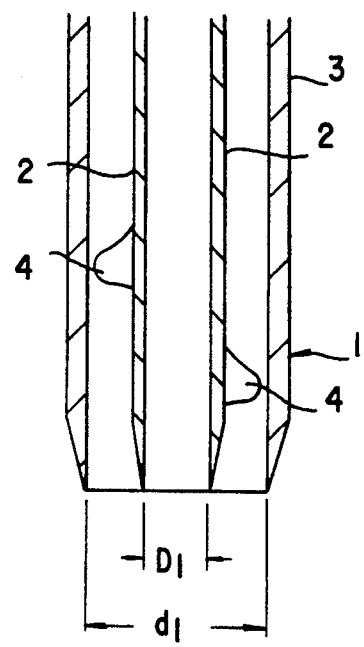
FIGS. 1(a) and 1(b) show a double layer nozzle used in the examples.

Hereinafter, concrete examples and reference examples of the present invention are shown, but the invention is not limited within the below-described examples.

EXAMPLE 1

Cellmatrix I-A (acid soluble collagen; concentration 3.0 mg/ml; pH 3.0; Nitta Gelatin Inc.) 8 parts by volume was mixed with Ham's F 12 culture medium (10 times concentration) 1 part by volume, a reconstitution buffer solution (prepared by dissolving 2.2 g of sodium hydrogencarbonate and 4.77 g of HEPES in 100 ml of a 50 mM aqueous sodium hydroxide solution) 1 part by volume, and fetal calf serum 1 part by volume, and to the obtained mixed collagen solution was added a mouse mammary tumor cell line suspension 1 part by volume. The resulting solution was kept at 4° C. to give a collagen solution containing animal cells which was used as an inner solution.

Figure 1B:
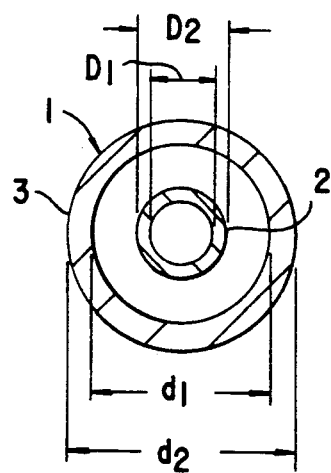

A 1% aqueous solution of sodium alginate was used as an outer solution (coating-forming agent solution). By using a double orifice nozzle 1 having the same center as shown in FIG. 1, the outer solution was continuously fed from the outer tube 3, while the inner solution was intermittently fed from the inner tube 2, and the resulting drops were dropped into a 1% aqueous calcium chloride dihydrate solution (hardening solution) to form beads. After standing for 10-20 minutes, the beads were recovered by filtration using a nylon mesh and washed in Hanks' solution without calcium and magnesium to remove excess calcium chloride.

In this procedure, the dropping rate was 50 drops per minute and the total volume of the outer and inner solution 30 μl per drop and the volume ratio between the inner solution and outer solution 1 to 2. As shown in FIG. 1(a) and (b), for the nozzle 1 the inner tube 2 and the outer tube 3 are arranged in a mode having the same center hold. The internal diameter ($D_1$) and external diameter ($D_2$) of the inner tube 2 are 0.30 and 0.50 mm, respectively, and the corresponding diameters ($d_1$) and ($d_2$) of the outer tube 3 are 0.85 and 1.20 mm, respectively. In FIG. 1, 4 shows a supporting material for the tube center.

Next, the beads were warmed in Dulbecco's modified Eagle's medium for 60 minutes at 37° C. to undergo gelation of the inner collagen, in which cells were dispersed, to obtain alginate-coated collagen gel beads, whose average diameter was approximately 3.5 mm.

The obtained collagen gel beads which contain cells and were covered with alginic acid were subjected to shaking culture using Dulbecco's modified Eagle's medium containing 10% fetal calf serum and 10 mM HEPES in a flask maintained at 37° C.

REFERENCE EXAMPLE 1

When the double-layer gel beads obtained from example 1 is soaked in Hanks' solution without calcium and magnesium and with 10 mM EDTA for 7-15 minutes, the outer layer alginate was dissolved to give beads of a cell-containing collagen gel alone, which did not contain a protective coating. With these collagen beads, culture was carried out in the same manner as in example 1.

The collagen beads without a protective coating (reference example 1) shrank from about 1.6 mm to about 1.1 mm in average diameter after cultivation for 12 days. In contrast, the alginate-coated collagen gel beads (example 1) showed no change in the average diameter even on the 12th day after cultivation was initiated.

Table 1 presents the results obtained from measurements of cell number in both the beads. Cell proliferation is maintained in the alginate-coated collagen gel beads, whereas cell proliferation reaches the uppermost limit on the 7th day after cultivation has been initiated in beads without a protective coating. Additionally, a dendritic outgrowth was observed for mouse mammary tumor cell line in the alginate-coated collagen gel beads. This shows that the collagen gel is a very suitable supporting substrate for the cultivation of anchorage-dependent cells.

TABLE 1

| Cultivating days | DNA (μg/bead) | |
|---|---|---|
| | Reference Example 1 | Example 1 |
| 0 | 0.07 | 0.07 |
| 5 | 0.20 | 0.33 |
| 7 | 0.69 | 1.01 |
| 10 | 0.60 | 1.12 |
| 12 | 0.68 | 1.26 |

EXAMPLE 2

Figure 2:
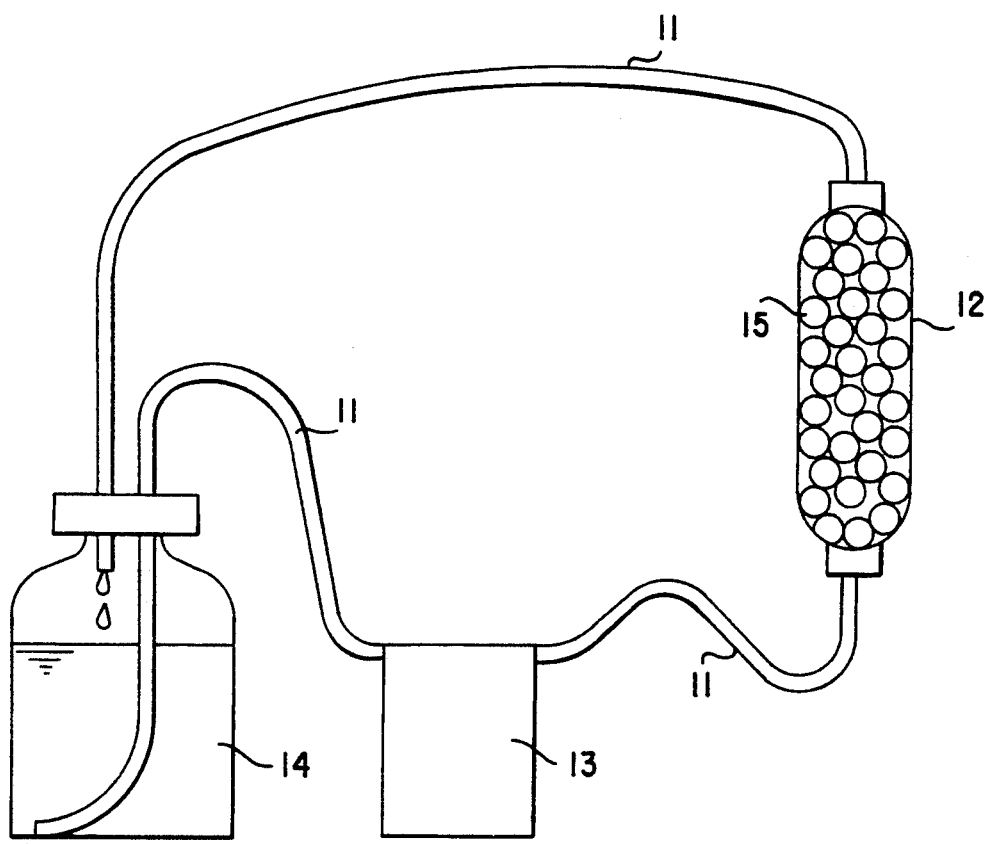
FIG. 2 is a model view of an apparatus for large-scale cultivation used in the examples.

The same as in example 1, except that a mouse fibroblast cell line was used instead of a mouse mammary tumor cell line. The same treatment as in example 1 gave alginate-coated collagen gel beads containing cells. As seen in FIG. 2, 1000 pieces of beads 15 (volume was about 40 cm$^3$) were packed in a polystyrene column 12. As seen in FIG. 2, the column 12 was connected with tube 11 and the culture medium 14 was circulated by the pump 13. The apparatus shown in FIG. 2 was mounted on a $CO_2$ incubator maintained at 37° C. and the culture medium 14 used in example 1 was continuously circulated for cultivation. The cells were able to be cultivated for about 1 month without bead destruction, and thus, confirming the strong physical character of the beads. The culture medium exchange was carried out in a manner that the amount of the circulating culture medium was about 1 ml per minute. The amount of culture medium used was 50 ml per day at the beginning and 500 ml per day at the last, and a bottle for the medium was exchanged every day.

That the cells can be cultivated for a long period in the cultivation method using a column as shown in example 2, shows such effects as the below-described (A)-(C) and is very useful as a system for large-scale cultivation of animal cells.

(A) Culture medium exchange can be carried out very easily.

(B) Recovery of products from cells can be carried out easily and effectively.

(C) Large-scale cultivation can be carried out in a compact space.

EXAMPLE 3

The same as in example 1, except the cells were replaced by a mouse fibroblast cell line and the inner solution and the outer solution were continuously, at the same time, pushed out. A procedure the same as that for example 1 gave a product of a double layer noodle shape, which was washed and then warmed at 37° C. for 1 hour to cause gelation of the inner collagen solution. This gel was a double layer gel of a noodle shape having a diameter of about 1 mm.

The product obtained was subjected to static cultivation in a $CO_2$ incubator at 37° C. using the culture medium used in example 1.

On the second day of cultivation, developing fibroblasts were recognized.

Industrial Applicability

The method for the large-scale cultivation of animal cells according to the described invention, can be applied for both anchorage-dependent cells and anchorage-independent cells. In particular, the effect is significant if the method is applied for the cultivation of anchorage-dependent cells. Even in the case of anchorage-dependent cells, if cell growth is not disturbed by collagen shrinkage or if large shrinkage does not take place with progressing proliferation, a coating-forming agent can be selected without attention to joining the collagen gel with the protective coating. For example, an agent like agarose, which has a weaker joining force compared with that of alginic acid, etc., can be used as a coating-forming agent.

According to the method for the large-scale cultivation of animal cells, animal cells cultivated in large quantities can be obtained within a short period of time and in a small space. Also, various kinds of cell-produced materials can be obtained with high efficiency. Examples of such cell-produced materials include vaccines, enzymes, hormones, antibodies, nucleic acids, and so forth. Also, the cell line itself can be used, by being greatly proliferated, for several kinds of purposes.

If the protective coating is a calcium alginate coating, cells can be recovered after cultivation by removing the calcium ion with a chelate agent such as EDTA and EGTA, etc., thereby dissolving the alginate coating. The inner collagen gel can be decomposed by using collagenase, etc., so that the cell can be recovered alive.

To recover a material produced from the cell, it is sufficient to collect the material together with a culture solution, which comes into the culture solution passing through the protective coating.

When a method for large-scale cultivation of animal cells according to the present invention is carried out, the animal cell, which is embedded in collagen gel covered by a protective coating, is not especially limited but, for example, can be obtained by a method for making supporting substrata for the cultivation according to the present invention. According to this method, an animal cell of that kind can be arranged with high efficiency and only an aqueous solution can be used without using an organic solvent. In addition, contamination from outside is easily prevented and a sterile condition is easily maintained.

We claim:

1. A method for the large-scale cultivation of animal cells, comprising:
   suspending animal cells in a collagen solution;
   expelling said collagen solution with said animal cells from an inner tube of a double layer nozzle while simultaneously expelling a coating solution containing sodium alginate from an outer tube of said double layer nozzle, whereby said collagen solution is coated by said coating solution to form a coated collagen solution;
   adding said coated collagen solution to a hardening solution containing a calcium salt, thereby hardening said coating solution to form a protective coating;
   warming said coating collagen solution such that said collagen solution undergoes gelation to form a coated collagen gel embedded with said animal cells and coated with said protective coating;
   suspending said coated collagen gel in a cultivating solution.

2. The method of claim 1, wherein the protective coating covers at least 50% of the collagen surface.

* * * * *